(12) United States Patent
Werve

(10) Patent No.: US 7,043,998 B2
(45) Date of Patent: May 16, 2006

(54) CERAMIC INSPECTION SYSTEM

(75) Inventor: Michael E. Werve, Modesto, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/957,179

(22) Filed: Sep. 30, 2004

(65) Prior Publication Data

US 2006/0070453 A1    Apr. 6, 2006

(51) Int. Cl.
*G01L 1/24* (2006.01)

(52) U.S. Cl. ..................................... 73/800

(58) Field of Classification Search ............... 73/825, 73/800; 356/237.1, 241.1; 242/538.2; 33/1 M
See application file for complete search history.

(56) References Cited

U.S. PATENT DOCUMENTS

| | | | | |
|---|---|---|---|---|
| 3,680,805 A | * | 8/1972 | Stewart et al. ........... | 242/538.2 |
| 4,925,304 A | * | 5/1990 | Updike ..................... | 356/241.1 |
| 5,699,153 A | * | 12/1997 | Takamoto et al. ........ | 356/237.1 |
| 6,082,010 A | * | 7/2000 | Lee ............................. | 33/1 M |
| 6,405,602 B1 | | 6/2002 | Itou et al. | |
| 6,480,010 B1 | | 11/2002 | Ikuta et al. | |
| 6,605,807 B1 | * | 8/2003 | Safai ........................ | 250/341.1 |
| 6,729,190 B1 | * | 5/2004 | Boyko et al. ................. | 73/825 |

* cited by examiner

*Primary Examiner*—Max Noori
*Assistant Examiner*—Octavia Davis
(74) *Attorney, Agent, or Firm*—Eddie E. Scott; Alan H. Thompson

(57) ABSTRACT

A system for inspecting a ceramic component. The ceramic component is positioned on a first rotary table. The first rotary table rotates the ceramic component. Light is directed toward the first rotary table and the rotating ceramic component. A detector is located on a second rotary table. The second rotary table is operably connected to the first rotary table and the rotating ceramic component. The second rotary table is used to move the detector at an angle to the first rotary table and the rotating ceramic component.

16 Claims, 5 Drawing Sheets

CERAMIC INSPECTION SYSTEM

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to an inspection system and more particularly to a ceramic inspection system.

2. State of Technology

U.S. Pat. No. 6,405,602 provides the following state of technology information, "Inspections by compression on a ceramic structure, such as a honeycomb structure, is performed by applying hydrostatic pressure on the ceramic structure."

U.S. Pat. No. 6,480,010 provides the following state of technology information, "internal defects such as microcracks or other defects which may occur in a piezoelectric ceramic device such as an oscillator, a filter, or other such device, which defects affect the qualities and characteristics of the piezoelectric ceramic device a method of inspecting a piezoelectric ceramic device includes the steps of heating and increasing the temperature of a piezoelectric ceramic device to an increased temperature that is in the vicinity of a maximum temperature at which the piezoelectric ceramic device, when the temperature of the device is returned to ordinary temperature, is returned to substantially the same piezoelectric characteristic as that before heating, measuring at least one of the piezoelectric phase characteristic and the impedance characteristic of the piezoelectric ceramic device while the device is heated and the temperature thereof is increased, comparing at least one of the measured piezoelectric phase characteristic and the measured impedance characteristic with a standard characteristic, and detecting the presence or absence of an internal defect of the piezoelectric ceramic device based on results of the step of comparing."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for the quick visual inspection of ceramic components using a high intensity white light source. The system of the present invention can be used for the inspection of ceramic parts in production facilities. These inspections can be carried out before and after firing and after finishing operations. The present invention also provides a system for the quality assurance inspection of ceramic parts prior to their use in assembly operations.

The ceramic component is positioned on a first rotary table. The first rotary table rotates the ceramic component. Light is directed toward the first rotary table and the rotating ceramic component. A detector is located on a second rotary table. The second rotary table is operably connected to the first rotary table and the rotating ceramic component. The second rotary table is used to move the detector at an angle to the first rotary table and the rotating ceramic component. In one embodiment the detector is a camera detector that is used to scan the rotating ceramic component. The scan of the rotating ceramic component is used to produce a visual image of the ceramic component.

One embodiment of the present invention provides an apparatus for inspecting a ceramic component. The apparatus includes a light table with a first rotary table operably connected to the light table and a second rotary table operably connected to the light table. A light source is operably connected to the first rotary table and the second rotary table. A detector is operably connected to second rotary table. Light is directed toward the first rotary table and the rotating ceramic component. The second rotary table is used to move the detector at an angle to the first rotary table and the rotating ceramic component. In one embodiment the detector is a camera detector that is used to scan the rotating ceramic component.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
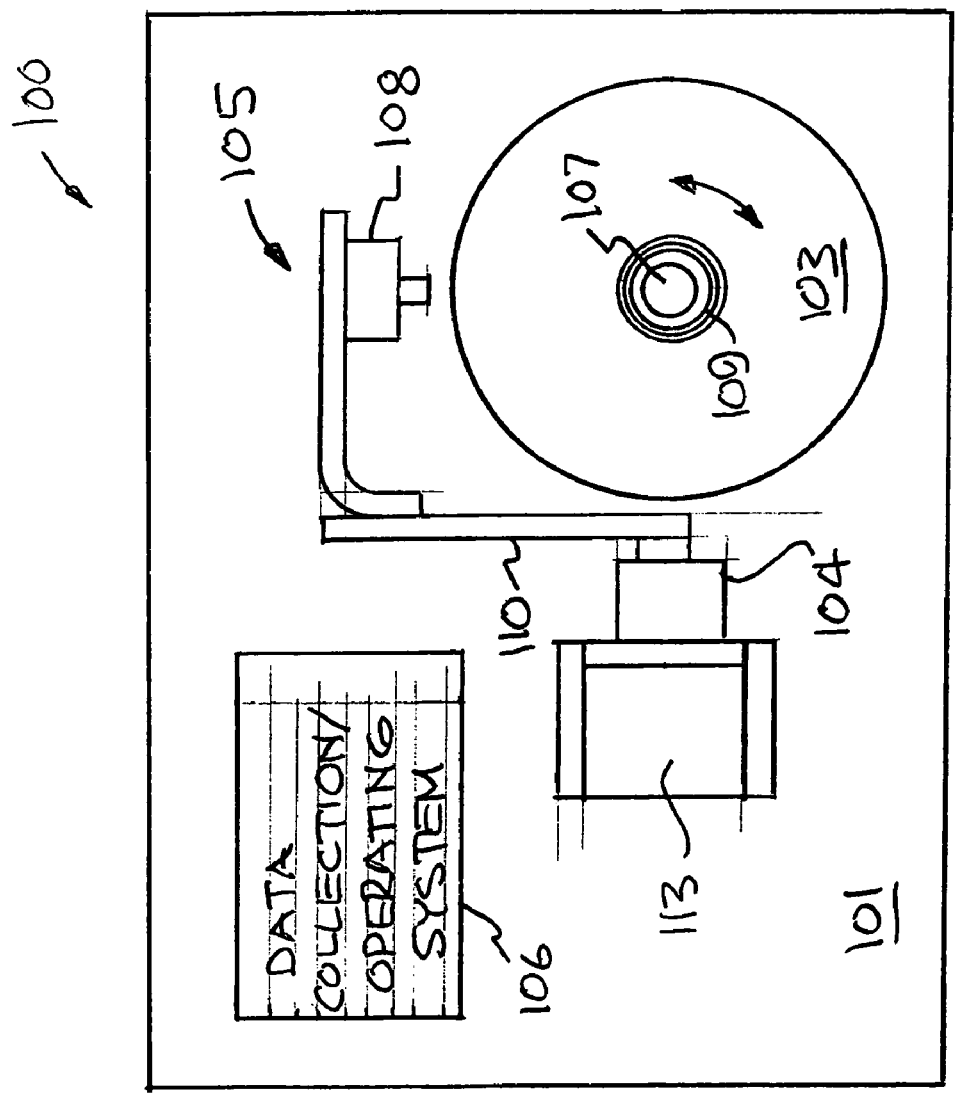
FIG. 1 is a plan view of one embodiment of a system constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

As part of life extension program at the Lawrence Livermore National Laboratory, ceramic components are inspected for defects. Historically these inspections were performed with X-ray technology, requiring the part to be taken from the factory floor to a x-ray facility for testing. With x-ray techniques a series of shots are required to show any potential defects.

The present invention provides a system for the quick visual inspection of ceramic components using a high intensity white light source. The system of the present invention can be used for the inspection of ceramic parts in production facilities. These inspections can be carried out before and after firing and after finishing operations. The present invention also provides a system for the quality assurance inspection of ceramic parts prior to their use in assembly operations.

The present invention provides a system that is faster, cheaper, and less invasive to the manufacturing process. In addition it is possible to inspect parts at various times during production to catch problems before further value added operations are performed.

The system of the present invention allows for fast real time inspection on the factory floor by the operator. Defects can be identified and documented immediately potentially identifying problems with production before other parts are processed, limiting scrap costs.

Referring now to FIG. 1, one embodiment of a system constructed in accordance with the present invention is illustrated. The system is designated generally by the reference numeral 100. The system 100 provides a system for the quick visual inspection of ceramic components using high intensity light.

The system comprises a light table 101 on which are light table components are mounted that perform the inspection of ceramic components or parts. There is a rotating platform 103 that is able to rotate in the directions of the double headed arrow. The component to be inspected will be mounted on the table 103 and is not shown in this figure. In the center of the platform 103 is a recess into which are mounted a light source 107 and a transparent shield 109 that protects the light source 107. The light source and shield can be raised or lowered into the recess of the platform 103 as will be shown in later figures. Adjacent the platform 103 is a robot arm 104 which is secured to the light table by bracket 113. The robot arm 104 has an extension arm 110 upon which is mounted the detection system 105. The detection system includes a detector 108 that can be moved in an arc perpendicular to the platform 103. The detector 108 comprises a light intensity detector and an interchangeable camera head. Also mounted upon the light table 101 is the data collection and operating system 106 that control the movement of both platform 103 and robot arm 104 during the scan of a ceramic component or part that is being inspected. The data collected will be presented to the operator of the scan by a visual image.

The ceramic component or part is positioned on a first rotary table and the component is rotated. Light is directed toward the first rotary table and the rotating component. A detector is positioned on a second rotary table that is perpendicular to the first rotary table and the rotating component. A detector is located on the second rotary table. The second rotary table moves the detector at an angle to the first rotary table and the rotating component. The detector is moved in an arc generally perpendicular to the first rotary table.

The light table 101 provides an automated two axis system for inspecting the ceramic components. The light table 101 has two rotary tables that operate together to define a scan pattern. The horizontal rotary table rotates the ceramic component. The vertical rotary table rotates the detector head. In combination the two rotary table axes define a hemisphere.

The system 100 of the present invention can be used for the inspection of ceramic parts in production facilities. These inspections can be carried out before and after firing and after finishing operations. The present invention also provides a system for the quality assurance inspection of ceramic parts prior to their use in assembly operations.

Figure 2:
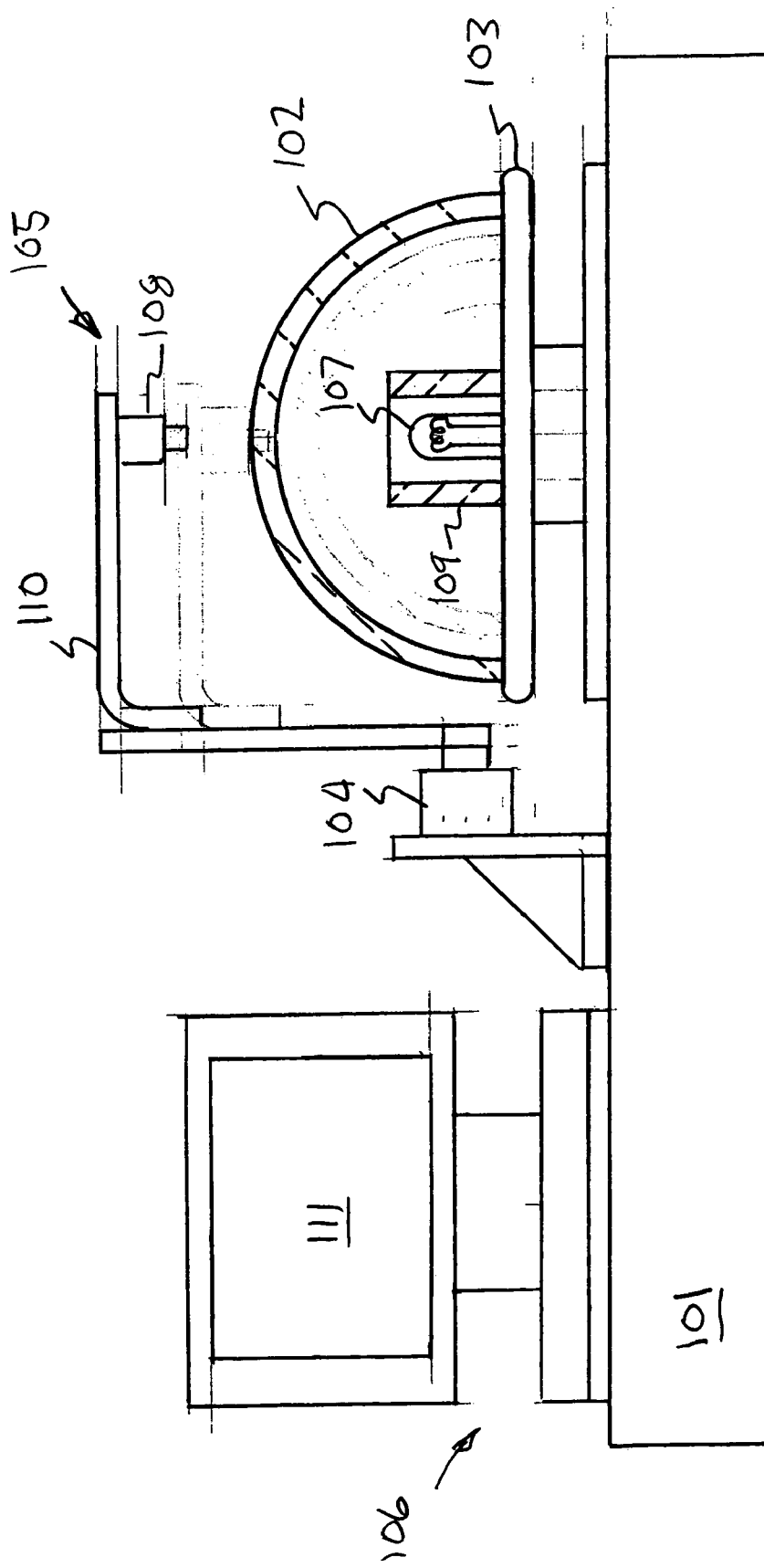
FIG. 2 shows a front elevation of the light table.

Referring now to FIG. 2, additional details of the system 100 for the quick visual inspection of ceramic components is shown. This figure shows a front elevation of the light table 101. Shown is the data collection and controls system 106, which include a screen 111 upon which will be displayed the data collected during a scan of a component such as the hemispherical part 102. As shown in FIG. 2, the system 100 is positioned for inspecting a ceramic casting 102 for defects. The inspection of the ceramic casting 102 can be done at various stages of manufacture.

Figure 3:
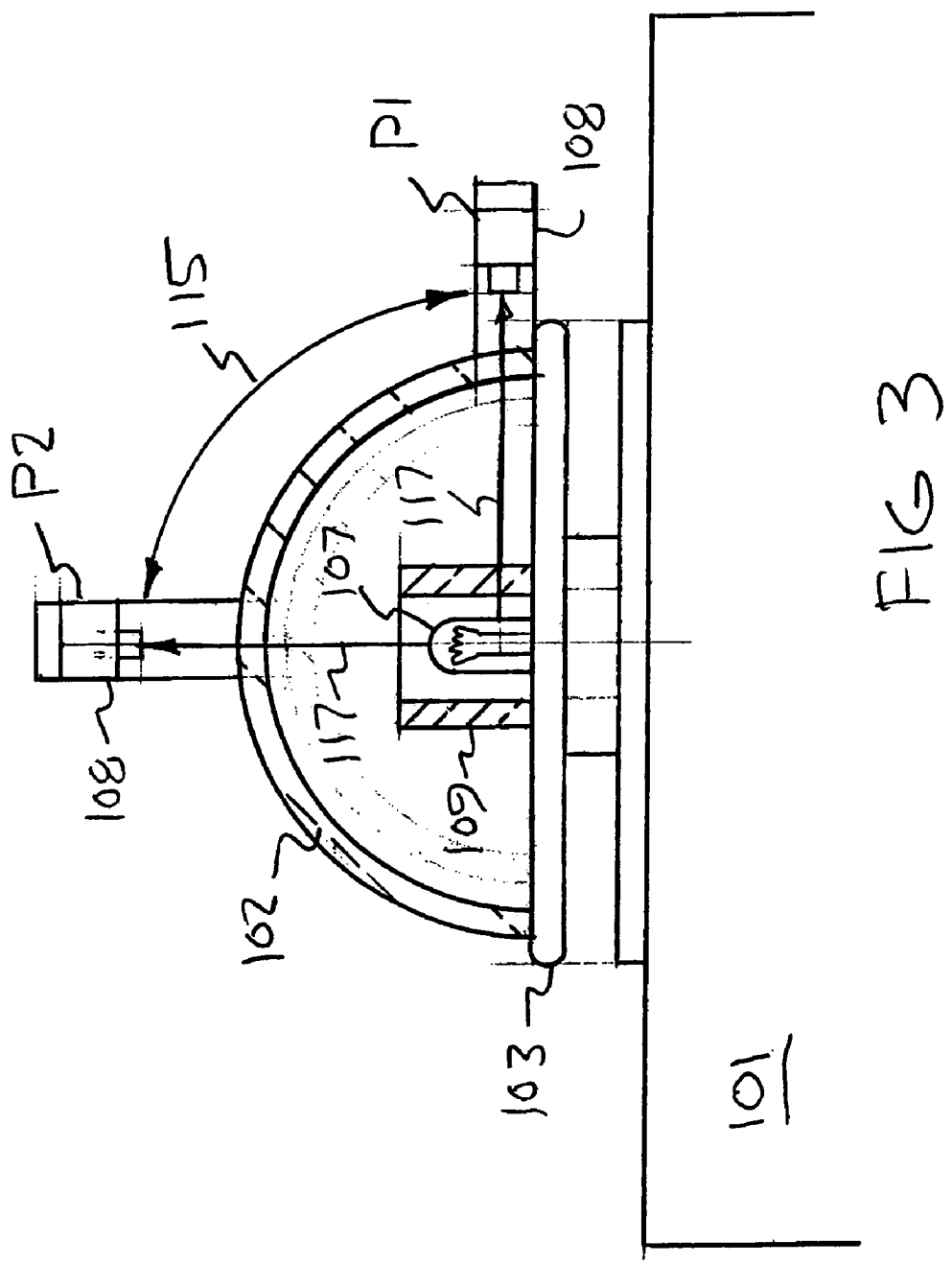
FIG. 3 shows a side elevation of the light table.
Figure 4:
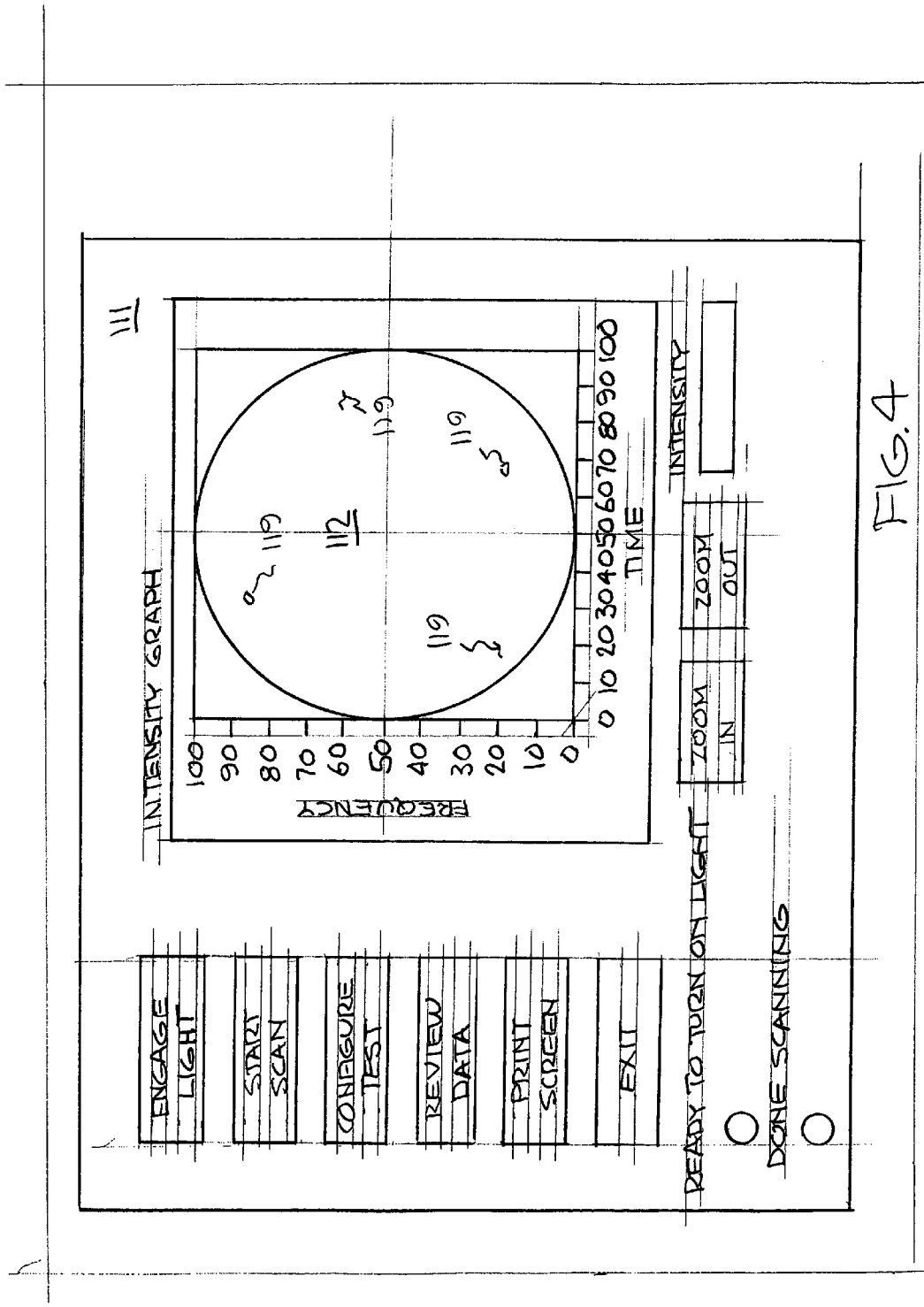
FIG. 4 shows a simulated view of a completed scan.

Referring now to FIG. 3, a side elevation of light table 103 is shown. The reference numerals fro items shown in FIG. 2 are also used in FIG. 3. As shown in FIG. 2 the light source 1107 and shield 109 are shown in the raised position ready for a scan. They are put in this position after the part to be inspected has been secured to platform 103, thereby preventing possible damage to those fragile parts during the installation of the part to be scanned. The detector 108 is shown here in tow different positions P1 and P2. The detector moves back and forth between these positions by traveling along arc 115. Also shown are the rays 117 from the light source 107 that penetrate the component 102 and are received by the detector 108. From the above description and figures it can be seen that by rotating the ceramic component or part 102 on platform 103 and swinging the detector 108 on arc 115 a complete hemispherical scan can be performed. All movement is under the control of system 106. The data is processed and displayed by system 106. A simulated depiction of this is shown in FIG. 4.

The system 100 utilizes a number of components mounted on the light table 101. The components include a first rotary table 103, a second rotary table 104, a detection system 105, a data collection/operating system 106, and a light source 107. The light table 101 is an automated two axis system. The ceramic component 102 is positioned on the first rotary table 103 and the component 102 is rotated. Light from the light source 107 is directed toward the first rotary table 103 and the rotating component 102.

The detection system 105 includes a detector 108 on the second rotary table 104 that moves in an arc perpendicular to the first rotary table 103 and the rotating ceramic component 102. The detector 108 is mounted on an arm 110 that is part of the second rotary table 104. The second rotary table 104 moves the detector 108 at an angle to the first rotary table 103 and the rotating ceramic component 102. The detector 108 comprises a light intensity detector and an interchangeable camera head. The detector 108 is moved in an arc generally perpendicular to the first rotary table 103 defining a hemisphere.

The light table 101 encloses the light source 107. The light source 107 is a high intensity broad band light source. In one specific embodiment it is an LTM Cinespace 575 W head with a 1200 W bulb. Power is supplied to the head by a 575/1200 W electronic ballast. The head develops a high-intensity broadband visible and invisible light, and the energy spectrum of the light is matched to the natural sunlight. The bulb is placed inside a glass shield for protection. The light from the light source 107 shines in a hemispherical pattern when extended through a hole in the table top. The light table 101 includes proximity sensor interlocks that prevent the light bulb from igniting when no part is in place.

The operating system/data collection system 106 utilizes the same software package. The detector 108 is focused to a 2, 4, or 6 mm viewing area. Reading is taken as often as desired and reconstructed by the software into C-scan presentation, also known as a Plan View. The intensity head can be switched out with the camera head and areas of interest macro or micro photographed as desired. These are linked by location within the software to the C-scan allowing the operator to point and click to switch between the two data sets.

The operating system/data collection system 106 produces a hemispherical scan of the ceramic part 102. This is accomplished by the second rotary table 104 moving the detector 108 at an angle to the first rotary table 103 and the rotating ceramic component 102. The detector 108 moves in an arc generally perpendicular to the first rotary table 103 defining a hemisphere. The operating system/data collection system 106 produces a visual image of the ceramic component 102 that can be observed on the screen 111.

Referring now to FIG. 4, an image of the ceramic component 102 is shown on the screen 111. This is a simulated view of the data collected fro a can of a ceramic component such as that shown in FIGS. 2 and 3 and indicated by reference numeral 102. A hemispherical scan of the ceramic component 102 by the detector 108 produces an image 112. The image 112 can be observed on the screen 111. The scan shows possible defects 119 such as cracks or voids.

Figure 5:
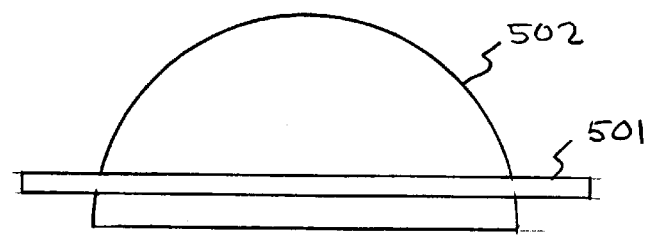
FIG. 5 shows an image of a ceramic component.
Figure 6:
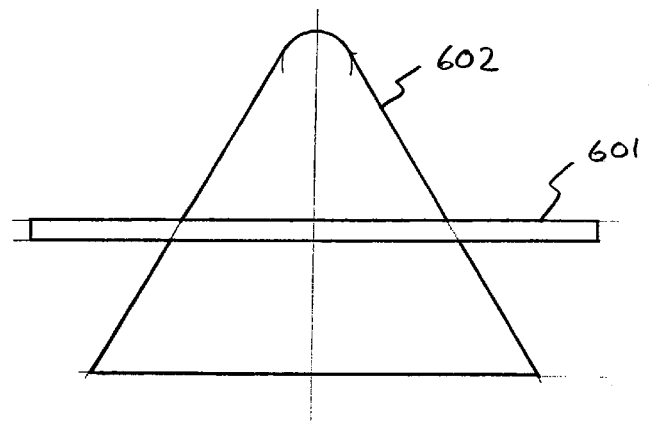
FIG. 6 illustrates the visual inspection of a small masked conical ceramic part.

A masked view of ceramic component 102 is shown in FIG. 5. The visual inspection of a small masked conical ceramic part is illustrated in FIG. 6. FIG. 5 shows a mask 501 covering part of the ceramic component 502. The purpose of the mask 501 is to obscure the true dimensions of the ceramic component which in some cases could be considered sensitive information. In FIG. 6, a conical part 602 is shown with a mask 601. The purpose of the mask 602 is to limit the amount of light that passes through the conical component. Too much light could affect the detector's ability to function correctly.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for inspecting a ceramic component having a concave inner surface and a convex outer surface, comprising:
    a light table,
    a rotary table operably connected to said light table,
    a light source operably connected to said rotary table, said light source positioned to direct light to the concave inner surface of the ceramic component,
    a detector, said detector positioned so that said detector receives light from the convex outer surface of the ceramic component to detect light that passes through the ceramic component from the concave inner surface to the convex outer surface, and
    a robot arm operably connected to said rotary table that moves said detector in an arc along the convex outer surface of the ceramic component.

2. The apparatus for inspecting a ceramic component of claim 1 wherein said light source is a high intensity light source.

3. The apparatus for inspecting a ceramic component of claim 1 wherein said light source is a high intensity broad band light source.

4. The apparatus for inspecting a ceramic component of claim 1 wherein said detector includes a camera head.

5. The apparatus for inspecting a ceramic component of claim 1 wherein said rotary table and said robot arm are positioned at an angle to each other.

6. The apparatus for inspecting a ceramic component of claim 1 wherein said rotary table and said robot arm are positioned perpendicular to each other.

7. An apparatus for inspecting a ceramic component having a concave inner surface and a convex outer surface, comprising:
    a support means,
    rotary table means operably connected to said support means for rotating the ceramic component,
    light source means operably connected to said rotary table for directing light toward said rotary table and the rotating ceramic component, said light source means positioned to direct light to the concave inner surface of the ceramic component,
    detector means for producing a scan of the rotating ceramic component, and
    robot means operably connected to said rotary table for moving said detector in an arc along the convex outer surface of the ceramic component.

8. The apparatus for inspecting a ceramic component of claim 7 wherein said detector means is a camera detector that produces a scan of the rotating ceramic component.

9. The apparatus for inspecting a ceramic component of claim 8 including means for using said scan to produce a visual image of the ceramic component.

10. A method for inspecting a ceramic component having a concave inner surface and a convex outer surface, comprising the steps of:
    positioning the ceramic component on a rotary table and rotating the ceramic component,
    directing light toward said first rotary table and the rotating ceramic component and onto the concave inner surface of the ceramic component,
    positioning a detector on a robot that is operably connected to said rotary table and the rotating ceramic component, said detector positioned so that said detector receives light from the convex outer surface of the ceramic component to detect light that passes through the ceramic component from the concave inner surface to the convex outer surface, and
    using said robot to move said detector at an angle to said rotary table and the rotating ceramic component, said robot moving said detector in an arc along the convex outer surface of the ceramic component to produce a scan of the rotating ceramic component.

11. The method for inspecting a ceramic component of claim 10 wherein said step of directing light toward said rotary table and the rotating ceramic component comprises directing high intensity light toward said first rotary table and the rotating ceramic component.

12. The method for inspecting a ceramic component of claim 11 wherein said step of directing light toward said rotary table and the rotating ceramic component comprises directing high intensity broad band light toward said first rotary table and the rotating ceramic component.

13. The method for inspecting a ceramic component of claim 11 wherein said step of using said robot to move said detector at an angle to said rotary table and the rotating ceramic component comprises moving said detector in an arc generally perpendicular to said rotary table.

14. The method for inspecting a ceramic component of claim 11 wherein said step of using said robot to move said detector at an angle to said rotary table comprises using a camera detector to scan the rotating ceramic component.

15. The method for inspecting a ceramic component of claim 14 wherein said camera detector produces a scan of the rotating ceramic component.

16. The method for inspecting a ceramic component of claim 15 wherein said scan of the rotating ceramic component is used to produce a visual image of the ceramic component.

* * * * *